(12) United States Patent
Smith et al.

(10) Patent No.: US 10,646,718 B2
(45) Date of Patent: May 12, 2020

(54) COCHLEAR IMPLANTS AND MAGNETS FOR USE WITH SAME

(71) Applicant: ADVANCED BIONICS AG, Staefa (CH)

(72) Inventors: James George Elcoate Smith, Santa Clarita, CA (US); Sung Jin Lee, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 227 days.

(21) Appl. No.: 15/805,025

(22) Filed: Nov. 6, 2017

(65) Prior Publication Data

US 2018/0133486 A1     May 17, 2018

Related U.S. Application Data

(60) Provisional application No. 62/422,548, filed on Nov. 15, 2016.

(51) Int. Cl.
| | |
|---|---|
| *A61N 1/375* | (2006.01) |
| *A61N 1/05* | (2006.01) |
| *A61N 1/08* | (2006.01) |
| *A61N 1/372* | (2006.01) |
| *A61N 1/378* | (2006.01) |
| *A61N 1/36* | (2006.01) |

(52) U.S. Cl.
CPC .......... *A61N 1/375* (2013.01); *A61N 1/0541* (2013.01); *A61N 1/08* (2013.01); *A61N 1/086* (2017.08); *A61N 1/36038* (2017.08); *A61N 1/3787* (2013.01); *A61N 1/37217* (2013.01)

(58) Field of Classification Search
CPC ..... A61N 1/36038; A61N 1/0541; A61N 1/08
See application file for complete search history.

(56) References Cited

U.S. PATENT DOCUMENTS

| | | |
|---|---|---|
| 4,352,960 A | 10/1982 | Dormer et al. |
| 4,595,390 A | 6/1986 | Hakim et al. |
| 4,606,329 A | 8/1986 | Hough |
| 4,618,949 A | 10/1986 | Lister |
| RE32,947 E | 6/1989 | Dormer et al. |
| 5,290,281 A | 3/1994 | Tschakaloff |
| 5,755,762 A | 5/1998 | Bush |
| 5,824,022 A | 10/1998 | Zilberman et al. |
| 5,945,762 A | 8/1999 | Chen et al. |
| 6,178,353 B1 | 1/2001 | Griffith et al. |

(Continued)

FOREIGN PATENT DOCUMENTS

| | | |
|---|---|---|
| EP | 2117489 B1 | 5/2010 |
| EP | 2853287 A1 | 4/2015 |

(Continued)

OTHER PUBLICATIONS

U.S. Appl. No. 15/568,470, filed Oct. 21, 2017, 20180110986A1.

(Continued)

*Primary Examiner* — Joseph M Dietrich

(74) *Attorney, Agent, or Firm* — Henricks Slavin LLP

(57) ABSTRACT

A cochlear implant including a cochlear lead, a housing, a magnet apparatus located within the flexible housing and including a first partial disk shaped magnet member and a second partial disk shaped magnet member spaced apart from the first partial disk shaped magnet member, an antenna within the housing, and a stimulation processor.

20 Claims, 7 Drawing Sheets

(56) References Cited

U.S. PATENT DOCUMENTS

| | | |
|---|---|---|
| 6,190,305 B1 | 2/2001 | Ball et al. |
| 6,217,508 B1 | 4/2001 | Ball et al. |
| 6,227,820 B1 | 5/2001 | Jarvik |
| 6,292,678 B1 | 9/2001 | Hall et al. |
| 6,348,070 B1 | 2/2002 | Teissl et al. |
| 6,358,281 B1 | 3/2002 | Berrang et al. |
| 6,599,321 B2 | 7/2003 | Hyde, Jr. |
| 6,838,963 B2 | 1/2005 | Zimmerling |
| 7,091,806 B2 | 8/2006 | Zimmerling et al. |
| 7,190,247 B2 | 3/2007 | Zimmerling |
| 7,566,296 B2 | 7/2009 | Zimmerling et al. |
| 7,609,061 B2 | 10/2009 | Hochmair |
| 7,642,887 B2 | 1/2010 | Zimmerling |
| 7,680,525 B1 | 3/2010 | Damadian |
| 7,774,069 B2 | 8/2010 | Olson et al. |
| 7,856,986 B2 | 12/2010 | Darley |
| 7,881,800 B2 | 2/2011 | Daly et al. |
| 7,976,453 B2 | 7/2011 | Zimmerling et al. |
| 8,013,699 B2 | 9/2011 | Zimmerling |
| 8,118,725 B2 | 2/2012 | Zimmerling et al. |
| 8,255,058 B2 | 8/2012 | Gibson et al. |
| 8,340,774 B2 | 12/2012 | Hochmair et al. |
| 8,634,909 B2 | 1/2014 | Zimmerling et al. |
| 8,733,494 B1 | 5/2014 | Leigh |
| 8,734,475 B2 | 5/2014 | Ekvall et al. |
| 8,744,106 B2 | 6/2014 | Ball |
| 8,758,394 B2 | 6/2014 | Zimmerling et al. |
| 8,787,608 B2 | 7/2014 | Van Himbeeck et al. |
| 8,790,409 B2 | 7/2014 | Van den Heuvel et al. |
| 8,825,171 B1 | 9/2014 | Thenuwara et al. |
| 8,891,795 B2 | 11/2014 | Andersson |
| 8,897,475 B2 | 11/2014 | Ball et al. |
| RE45,701 E | 9/2015 | Zimmerling et al. |
| 9,126,010 B2 | 9/2015 | Shah et al. |
| 9,162,054 B2 | 10/2015 | Dalton |
| 9,227,064 B2 | 1/2016 | Duftner |
| 9,295,425 B2 | 3/2016 | Ball |
| 9,314,625 B2 | 4/2016 | Kasic, II et al. |
| 9,352,149 B2 | 5/2016 | Thenuwara et al. |
| RE46,057 E | 7/2016 | Zimmerling et al. |
| 9,392,382 B2 | 7/2016 | Nagl et al. |
| 9,420,388 B2 | 8/2016 | Ball |
| 9,549,267 B2 | 1/2017 | Nagl et al. |
| 9,615,181 B2 | 4/2017 | Nagl et al. |
| 9,656,065 B2 | 5/2017 | Tourrel et al. |
| 9,919,154 B2 | 3/2018 | Lee |
| 9,931,501 B2 | 4/2018 | Smyth |
| 10,300,276 B2 | 5/2019 | Lee et al. |
| 10,463,849 B2 | 11/2019 | Lee et al. |
| 2004/0012470 A1 | 1/2004 | Zimmerling et al. |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2006/0244560 A1 | 11/2006 | Zimmerling et al. |
| 2007/0053536 A1 | 3/2007 | Westerkull |
| 2007/0126540 A1 | 6/2007 | Zimmerling |
| 2008/0103350 A1 | 5/2008 | Farone |
| 2008/0195178 A1 | 8/2008 | Kuzma |
| 2009/0048580 A1 | 2/2009 | Gibson |
| 2009/0099403 A1 | 4/2009 | Zimmerling et al. |
| 2009/0134721 A1 | 5/2009 | Zimmerling |
| 2009/0248155 A1 | 10/2009 | Parker |
| 2009/0287278 A1 | 11/2009 | Charvin |
| 2010/0004716 A1 | 1/2010 | Zimmerling et al. |
| 2010/0046778 A1 | 2/2010 | Crawford et al. |
| 2010/0046779 A1 | 2/2010 | Crawford et al. |
| 2011/0009925 A1 | 1/2011 | Leigh et al. |
| 2011/0022120 A1 | 1/2011 | Ball et al. |
| 2011/0068885 A1 | 3/2011 | Fullerton et al. |
| 2011/0218605 A1 | 9/2011 | Cryer |
| 2011/0224756 A1 | 9/2011 | Zimmerling et al. |
| 2011/0255731 A1 | 10/2011 | Ball |
| 2011/0264172 A1 | 10/2011 | Zimmerling et al. |
| 2012/0296155 A1 | 11/2012 | Ball |
| 2013/0079749 A1 | 3/2013 | Overstreet et al. |
| 2013/0184804 A1 | 7/2013 | Dalton |
| 2013/0343588 A1 | 12/2013 | Karunasiri |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0121449 A1 | 5/2014 | Kasic et al. |
| 2014/0121586 A1 | 5/2014 | Bertrand et al. |
| 2014/0163692 A1 | 6/2014 | Van den Heuvel et al. |
| 2014/0343626 A1 | 11/2014 | Thenuwara et al. |
| 2015/0025613 A1 | 1/2015 | Nyberg, II et al. |
| 2015/0073205 A1 | 3/2015 | Ball et al. |
| 2015/0087892 A1 | 3/2015 | Tourrel et al. |
| 2015/0100109 A1 | 4/2015 | Feldman et al. |
| 2015/0265842 A1 | 9/2015 | Ridker |
| 2015/0367126 A1 | 12/2015 | Smyth |
| 2015/0374989 A1* | 12/2015 | Hazard ............... A61N 1/36036 607/57 |
| 2015/0382114 A1 | 12/2015 | Andersson et al. |
| 2016/0037273 A1 | 2/2016 | Gustafsson |
| 2016/0144170 A1 | 5/2016 | Gibson et al. |
| 2016/0205484 A1 | 7/2016 | Nagl et al. |
| 2016/0310737 A1 | 10/2016 | Tourrel et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0050027 A1 | 2/2017 | Andersson et al. |
| 2017/0078808 A1 | 3/2017 | Kennes |
| 2017/0156010 A1 | 6/2017 | Verma et al. |
| 2017/0239476 A1 | 8/2017 | Lee et al. |
| 2018/0028818 A1 | 2/2018 | Anderson et al. |
| 2018/0110985 A1 | 4/2018 | Walter |
| 2018/0110986 A1 | 4/2018 | Lee |
| 2018/0185634 A1 | 7/2018 | Smyth |
| 2019/0076649 A1 | 3/2019 | Lee et al. |
| 2019/0255316 A1 | 8/2019 | Lee et al. |

FOREIGN PATENT DOCUMENTS

| | | |
|---|---|---|
| EP | 2560730 B1 | 11/2016 |
| EP | 3138605 A1 | 3/2017 |
| WO | WO9858990 A1 | 12/1998 |
| WO | WO03081976 A2 | 10/2003 |
| WO | WO03092326 A1 | 11/2003 |
| WO | WO2004014269 A1 | 2/2004 |
| WO | WO2004014270 A1 | 2/2004 |
| WO | WO2007024657 A2 | 3/2007 |
| WO | WO2009124045 A1 | 10/2009 |
| WO | WO2009124174 A2 | 10/2009 |
| WO | WO2009149069 A2 | 12/2009 |
| WO | WO2010000027 A1 | 1/2010 |
| WO | WO2010083554 A1 | 7/2010 |
| WO | WO2011011409 A1 | 1/2011 |
| WO | WO2011109486 A2 | 9/2011 |
| WO | WO2011133747 A1 | 10/2011 |
| WO | WO2013043176 A1 | 3/2013 |
| WO | WO2013063355 A1 | 5/2013 |
| WO | WO2014011441 A1 | 1/2014 |
| WO | WO2014011582 A2 | 1/2014 |
| WO | WO2014046662 A1 | 3/2014 |
| WO | WO2014164023 A1 | 10/2014 |
| WO | WO2015065442 A1 | 5/2015 |
| WO | WO2016016821 A1 | 2/2016 |
| WO | WO2016190886 A1 | 12/2016 |
| WO | WO2016191429 A1 | 12/2016 |
| WO | WO2016207856 A1 | 12/2016 |
| WO | WO2017027045 A1 | 2/2017 |
| WO | WO2017027046 A1 | 2/2017 |
| WO | WO2017029615 A1 | 2/2017 |
| WO | WO2017034530 A1 | 3/2017 |
| WO | WO2017046650 A1 | 3/2017 |
| WO | WO2017087004 A1 | 5/2017 |
| WO | WO2017105510 A1 | 6/2017 |
| WO | WO2017105511 A1 | 6/2017 |
| WO | WO2017105604 A1 | 6/2017 |

(56) References Cited

FOREIGN PATENT DOCUMENTS

| WO | WO2017172566 A1 | 10/2017 |
|---|---|---|
| WO | WO2018217187 | 11/2018 |
| WO | WO2019160555 A1 | 8/2019 |

OTHER PUBLICATIONS

U.S. Appl. No. 15/703,808, filed Sep. 13, 2017.
Ju Hyun Jeon et al., "Reversing the Polarity of a Cochlear Implant Magnet After Magnetic Resonance Imaging," Auris Nasus Larynx, vol. 39, No. 4, pp. 415-417, Aug. 1, 2012.
Teissl et al., "Magentic Resonance Imaging and Cochlear Implants: Compatibility and Safety Aspects," Journal of Magnetic Resonance Imaging, Society For Magnetic Resonance Imaging, vol. 9, No. 1, pp. 26-38, Jan. 1, 1999.
U.S. Appl. No. 16/403,582, filed May 5, 2019.
U.S. Appl. No. 15/568,469, filed Oct. 21, 2017, 20180110985A1.
U.S. Appl. No. 15/770,207, filed Apr. 22, 2018, 20180304078 A1.
U.S. Appl. No. 16/060,383, filed Jun. 7, 2018, 20180369586 A1.
U.S. Appl. No. 15/591,054, filed May 9, 2017, U.S. Pat. No. 9,919,154.
U.S. Appl. No. 16/009,600, filed Jun. 15, 2018, 20180296826A1.
U.S. Appl. No. 16/403,582, filed May 5, 2019, 20190255316A1.
U.S. Appl. No. 15/568,470, filed Oct. 21, 2017, U.S. Pat. No. 10,300,276.
U.S. Appl. No. 16/101,390, filed Aug. 10, 2018, 20190046797 A1.
U.S. Appl. No. 15/703,808, filed Sep. 13, 2017, 20190076649 A1.
U.S. Appl. No. 15/805,025, filed Nov. 6, 2017, 20180133486 A1.
U.S. Appl. No. 16/499,311, filed Sep. 29, 2019.
U.S. Appl. No. 16/603,868, filed Oct. 9, 2019.

\* cited by examiner

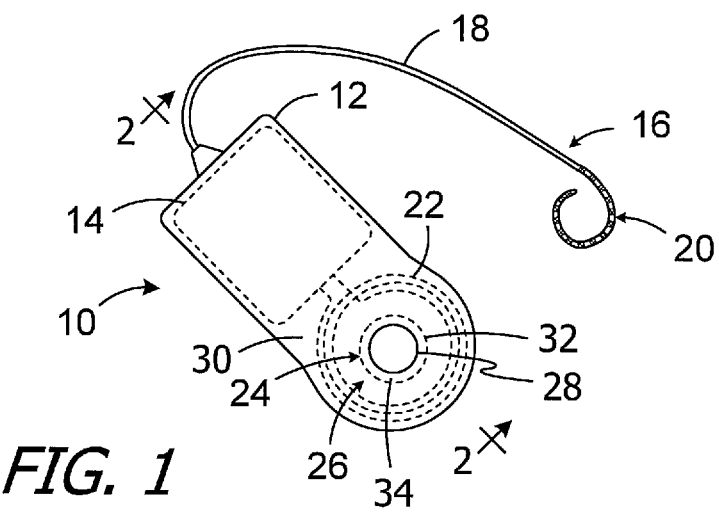
FIG. 1
Prior Art
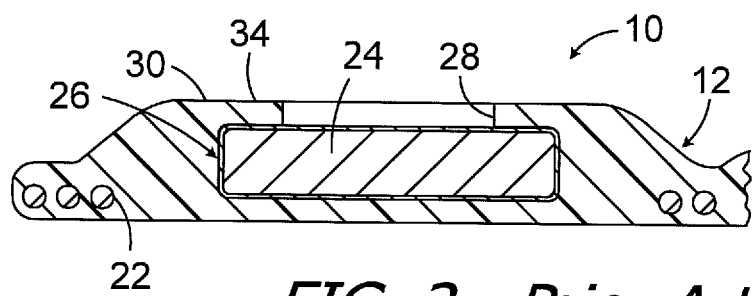
FIG. 2 - Prior Art

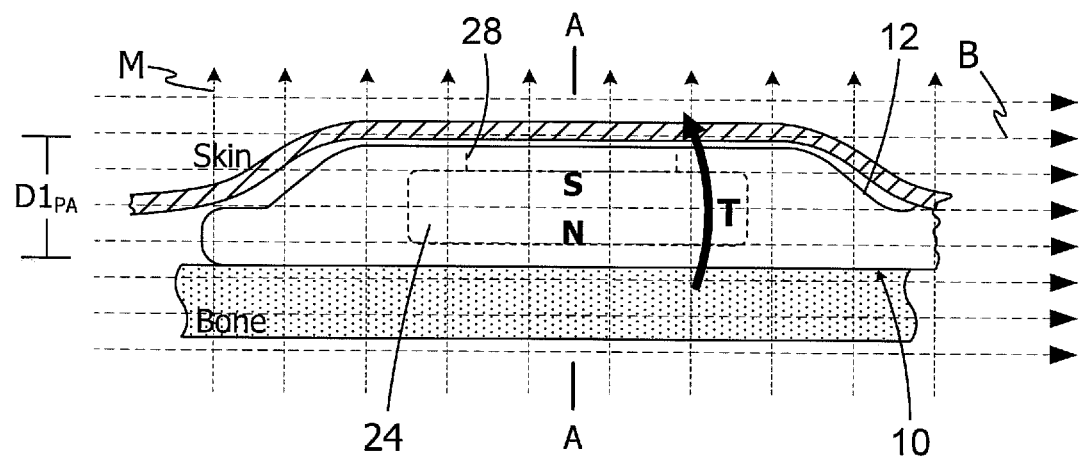
FIG. 3 - Prior Art
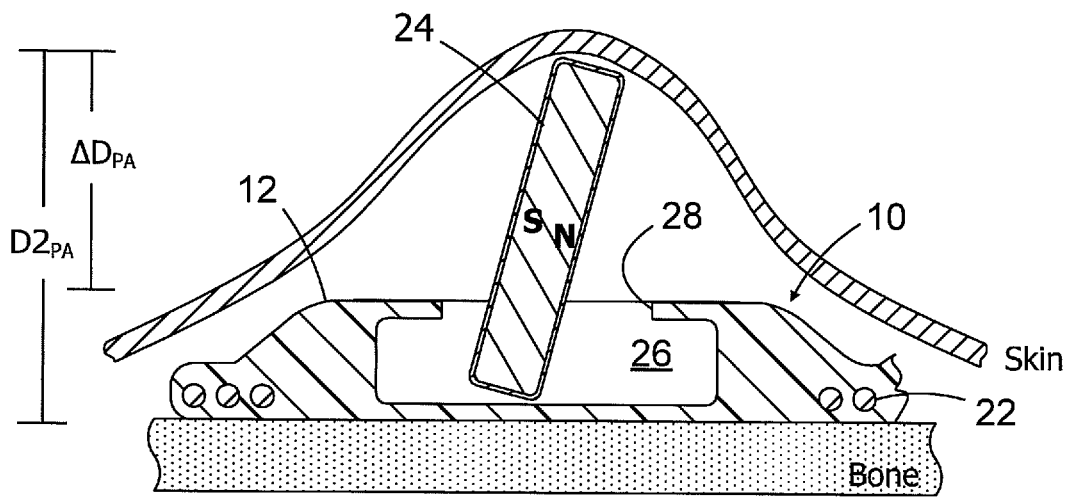
FIG. 4 - Prior Art

COCHLEAR IMPLANTS AND MAGNETS FOR USE WITH SAME

CROSS-REFERENCE TO RELATED APPLICATIONS

This application claims priority to U.S. Prov. App. Ser. No. 62/422,548, filed Nov. 15, 2016, which is incorporated herein by reference.

BACKGROUND

1. Field

The present disclosure relates generally to the implantable portion of implantable cochlear stimulation (or "ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Harmony™ BTE sound processor, the Naida™ CI Q Series sound processor and the Neptune™ body worn sound processor, which are available from Advanced Bionics.

As alluded to above, some ICS systems include an implantable cochlear stimulator (or "cochlear implant"), a sound processor unit (e.g., a body worn processor or behind-the-ear processor), and a microphone that is part of, or is in communication with, the sound processor unit. The cochlear implant communicates with the sound processor unit and, some ICS systems include a headpiece that is in communication with both the sound processor unit and the cochlear implant. The headpiece communicates with the cochlear implant by way of a transmitter (e.g., an antenna) on the headpiece and a receiver (e.g., an antenna) on the implant. Optimum communication is achieved when the transmitter and the receiver are aligned with one another. To that end, the headpiece and the cochlear implant may include respective positioning magnets that are attracted to one another, and that maintain the position of the headpiece transmitter over the implant receiver. The implant magnet may, for example, be located within a pocket in the cochlear implant housing.

One example of a conventional cochlear implant (or "implantable cochlear stimulator") is the cochlear implant 10 illustrated in FIGS. 1 and 2. The cochlear implant 10 includes a flexible housing 12 formed from a silicone elastomer or other suitable material, a processor assembly 14, a cochlear lead 16 with a flexible body 18 and an electrode array 20, and an antenna 22 that may be used to receive data and power by way of an external antenna that is associated with, for example, a sound processor unit. A cylindrical positioning magnet 24, with north and south magnetic dipoles that are aligned in the axial direction of the disk, is located within the housing 12. The magnet 24 is used to maintain the position of a headpiece transmitter over the antenna 22. The magnet 24 is also relatively thin in conventional cochlear implants in order to provide a relatively thin implant.

There are some instances where it is necessary to remove the magnet from a conventional cochlear implant, and then reinsert the magnet, in situ, i.e., with the cochlear implant accessed by way of an incision in the skin. To that end, the positioning magnet 24 is carried within an internal magnet pocket 26 and can be inserted into, and removed from, the housing pocket by way of a magnet aperture 28 that extends through the housing top wall 30. The positioning magnet 24 has a diameter of 10.5 mm and a thickness of 2.2 mm. The magnet 22 is larger than the magnet aperture 28, i.e., the outer perimeter of the magnet is greater than the perimeter of the magnet aperture. The portion of the top wall 30 between the aperture 28 and the outer edge 32 of the magnet 24 forms a retainer 34 that, absent deformation of the aperture and retainer, prevents the magnet from coming out of the housing 12. During installation and removal, the aperture 28 and retainer 34 are stretched or otherwise deformed so that the magnet 24 can pass through the aperture 28.

The present inventors have determined that conventional cochlear implants are susceptible to improvement. For example, removal and replacement of the implant magnet by way of the aperture may be required because some conventional cochlear implants are not compatible with magnetic resonance imaging ("MRI") systems. As illustrated in FIG. 3, the implant magnet 24 produces a magnetic field M in a direction that is perpendicular to the patient's skin and parallel to the axis A. This magnetic field direction is not aligned with, and may be perpendicular to (as shown), the direction of the MRI magnetic field B. The misalignment of the interacting magnetic fields M and B is problematic for a number of reasons. The dominant MRI magnetic field B (typically 1.5 Tesla or more) may generate a significant amount of torque T on the implant magnet 24. The torque T may be sufficient to deform the retainer 34, dislodge the implant magnet 24 from the pocket 26 and reorient the magnet in the manner illustrated in FIG. 4. In some instances, the implant magnet 24 may rotate 180 degrees, thereby reversing the N-S orientation of the magnet. The present inventors have determined that such reorientation (and reversal) may also occur if there is no aperture in the flexible housing, and the magnet is embedded within a closed pocket, due to the softness of the material (e.g., silicone) used to form the housing.

Reorientation of the magnet 24 can place significant stress on the dermis (or "skin"), which cause significant pain. Prior to rotation (FIG. 3), the distance $D1_{PA}$ between the skull bone below the cochlear implant and the skin above the implant is relatively small, i.e., slightly greater than the thickness of the implant magnet 24. The distance between the bone and skin greatly increases to distance $D2_{PA}$ when the implant magnet 24 rotates to the orientation illustrated in FIG. 4. In fact, because the diameter of the magnet 24 is far greater than the thickness, the difference $\Delta D_{PA}$ is significantly greater than the original distance $D1_{PA}$.

As alluded to above, magnet rotation may be avoided by surgically removing the magnet prior to the MRI procedure. However, in addition to the issues associated with the removal/replacement surgery, the presence of the magnet aperture 28 can lead to the formation of biofilm and can allow ingress of bacteria and microbes. Accordingly, the present inventors have determined that a solution which allows an MRI procedure to be performed without magnet removal/replacement surgery, thereby eliminating the need for the magnet aperture, would be desirable.

SUMMARY

A cochlear implant in accordance with one of the present inventions includes a cochlear lead, a housing, a magnet apparatus, located within the flexible housing, including a first partial disk shaped magnet member and a second partial disk shaped magnet member spaced apart from the first partial disk shaped magnet member, an antenna within the housing, and a stimulation processor. The present inventions also include systems with such a cochlear implant in combination with a headpiece, as well as systems with such a cochlear implant in combination with both a headpiece and a sound processor.

A cochlear implant in accordance with one of the present inventions includes a cochlear lead including a plurality of electrodes, a flexible housing including a magnet pocket, a top wall above the magnet pocket that does not include an opening into the magnet pocket, and a bottom wall below the magnet pocket that does not include an opening into the magnet pocket, a magnetic element, located within the magnet pocket, that defines a diameter, a thickness and the diameter to thickness ratio ("DtoT ratio") that is 2.5 or less, an antenna within the housing, and a stimulation processor. The present inventions also include systems with such a cochlear implant in combination with a headpiece, as well as systems with such a cochlear implant in combination with both a headpiece and a sound processor.

There are a number of advantages associated with such apparatus and systems. For example, when torque applied to the magnet apparatus by a strong magnetic field rotates the magnet apparatus, the increase in distance between the bone and skin (as well as the associated stress on the dermis and pain) will be far less than that associated with a conventional cochlear implant. As a result, surgical removal of the cochlear implant magnet prior to an MRI procedure, and then surgical replacement thereafter, is not required and the magnet aperture may be omitted.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 1 is a plan view of a conventional cochlear implant.

FIG. 2 is a section view taken along line 2-2 in FIG. 1.

FIG. 3 is a section view showing the conventional cochlear implant as an MRI magnetic field is being applied.

FIG. 4 is a section view showing the result of the application of the MRI magnetic field to the conventional cochlear implant.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 5:
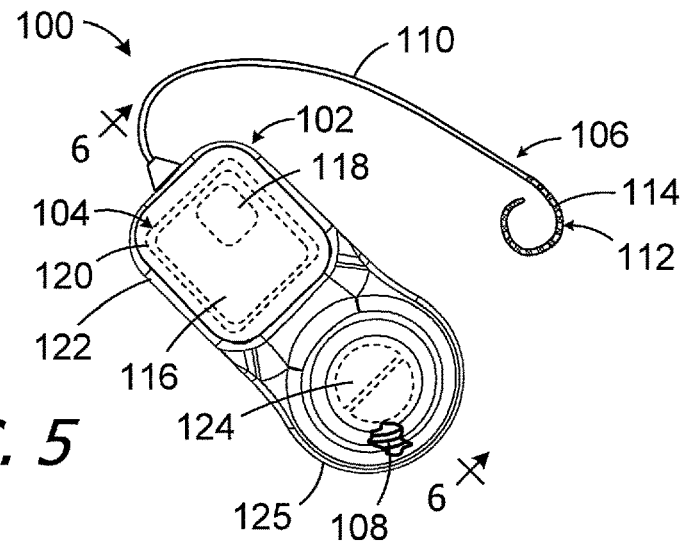
FIG. 5 is a plan view of a cochlear implant in accordance with one embodiment of a present invention.
Figure 6:
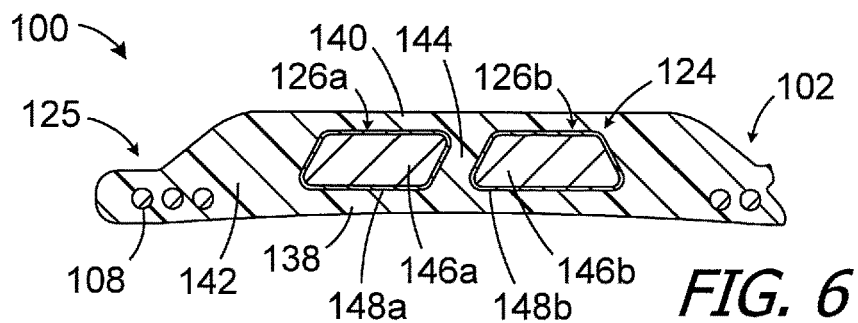
FIG. 6 is a section view taken along line 6-6 in FIG. 5.
Figure 7:
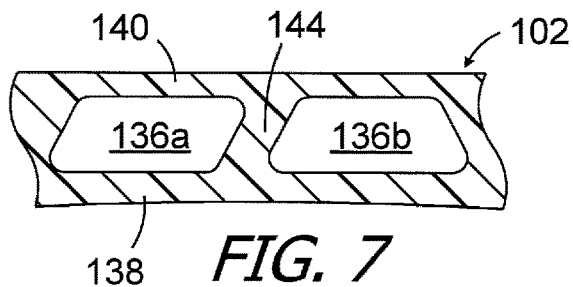
FIG. 7 is a portion of FIG. 6 with the magnet apparatus removed.
Figure 8:
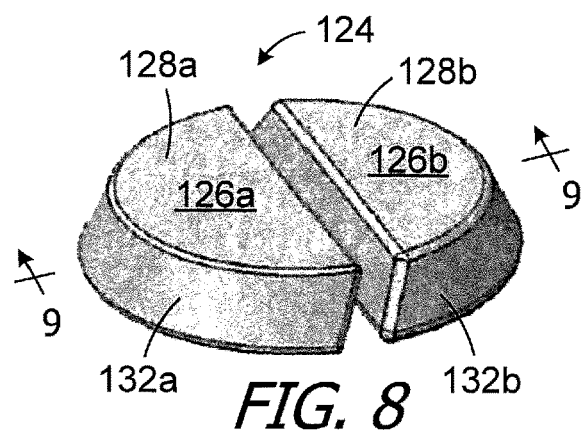
FIG. 8 is a perspective view of a portion of the cochlear implant illustrated in FIG. 5.
Figure 9:
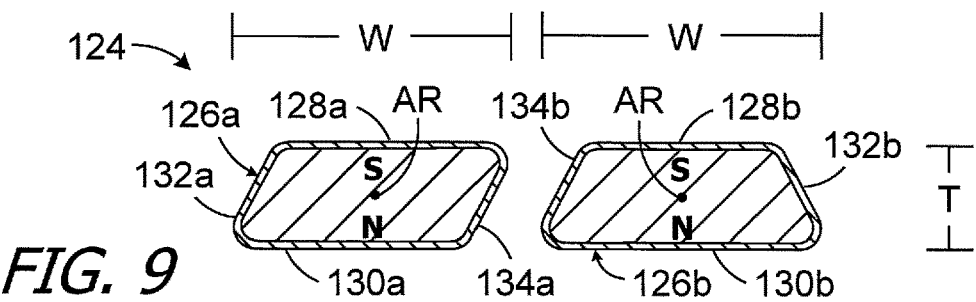
FIG. 9 is a section view taken along line 9-9 in FIG. 8.

One example of a cochlear implant (or "implantable cochlear stimulator") in accordance with the present inventions is the cochlear implant 100 illustrated in FIGS. 5-9. Referring first to FIG. 5, the exemplary cochlear implant 100 includes a resilient flexible housing 102 formed from a silicone elastomer or other suitable material (e.g., with a hardness from 50 to 70 Shore A), a processor assembly 104, a cochlear lead 106, and an antenna 108 that may be used to receive data and power by way of an external antenna that is associated with, for example, a sound processor unit. The cochlear lead 106 may include a flexible body 110, an electrode array 112 at one end of the flexible body 102, and a plurality of wires (not shown) that extend through the flexible body from the electrodes 114 (e.g., platinum electrodes) in the array 112 to the other end of the flexible body. The exemplary antenna 108 is a coil antenna with one or more loops (or "turns"), and three loops are shown in the illustrated embodiment. The exemplary processor assembly 104, which is connected to the electrode array 112 and antenna 108, includes a printed circuit board 116 with a stimulation processor 118 that is located within a hermetically sealed case 120. The stimulation processor 118 converts stimulation data into stimulation signals that stimulate the electrodes 114 of the electrode array 112. The hermetically sealed case 120 is located within a processor portion 122 of the housing 102. A positioning magnet apparatus 124 is located within an antenna portion 125 of the housing 102. The magnet apparatus 124, which is used to maintain the position of a headpiece transmitter over the antenna 108, is centered relative to the antenna 108.

Turning to FIGS. 6-9, the exemplary magnet apparatus 124 includes first and second magnet portions 126a and 126b which have complementary shapes that together define the overall shape of the magnet apparatus. In the illustrated implementation, the magnet apparatus 124 has an overall frustoconical shape with a circular (or substantially circular) bottom and a circular (or substantially circular) top. The first and second magnet portions 126a and 126b each have a partial disk shape and, to that end, have respective partial disk shaped top surfaces 128a and 128b, partial disk shaped bottom surfaces 130a and 130b, outer side surfaces 132a and 132b, and inner side surfaces 134a and 134b that face one another. As used herein, a "partial disk shape" includes an arcuate edge of about 180 degrees (i.e., 180 degree±5%) and a non-arcuate edge that extends from one end of the arcuate edge to the other. In a cross-section extending through the inner side surface 134a and 134b, the first magnet portion 126a has parallelogram shape (with rounded corners) and the second magnet portion 126b has a trapezoid shape (with rounded corners). The first and second magnet portions 126a and 126b also have the same N-S orientation.

Figure 10:
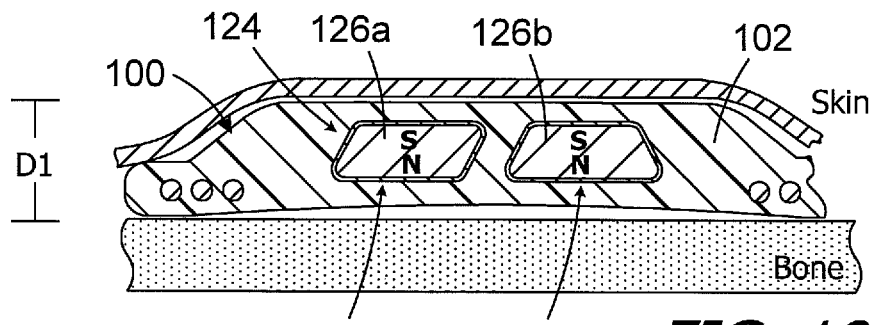
FIG. 10 is a section view of the cochlear implant illustrated in FIG. 5 prior to the application of a MRI magnetic field.
Figure 11:
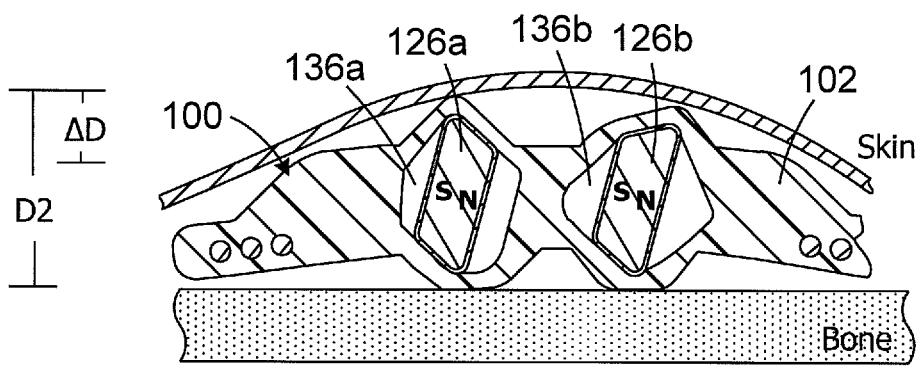
FIG. 11 is a section view showing the result of the application of the MRI magnetic field to the cochlear implant illustrated in FIG. 10.

The exemplary first and second magnet portions 126a and 126b are respectively located within magnet pockets 136a and 136b in the housing antenna portion 125 which, in their unstressed states, have sizes and shapes corresponding to those of the first and second magnet portions. In the illustrated implementation, the magnet portions 126a and 126b are embedded within the housing 102 such that, when the cochlear implant 100 is in its flat state (FIG. 6) without any rotation of the magnet portions 126a and 126b, the magnet portions are in contact with the resilient material that forms the housing and there are no gaps between the magnet portions and the inner surfaces of the magnet pockets. In particular, the magnet pockets 136a and 136b are surrounded by, and defined by, a bottom wall 138 that is located under the magnet pockets (in the illustrated orientation), a top wall 140 that is located above the magnet pockets (in the illustrated orientation), a side wall 142 that is lateral of, and extends around, the magnet pockets and a divider wall 144 that is located between the magnet pockets as well as between the magnet portions 126a and 126b. There are no openings in the bottom wall 138 or the top wall 140 for removal of the magnet apparatus 124. It should also be noted that the silicone elastomer (or other suitable resilient material) is stiff enough to maintain the magnet portions 126a and 126b in the illustrated orientation, in the absence of a strong external magnet filed, despite the N-N and S-S polar alignment of the magnet portions. The resilient material will, however, allow the magnet portions 126a and 126b to rotate in the manner described below with reference to FIGS. 10 and 11 when exposed to a MRI magnetic field. In some instances, a lubricious coating may be applied to the exterior of the magnet portions 126a and 126b to reduce the friction between magnet portions and the housing 102, thereby reducing torque. Suitable lubricious coatings include hydrophilic hydrogel and diamond-like carbon, both of which would significantly reduce friction and are biocompatible.

Although the present inventions are not so limited, the magnet portions 126a and 126b of the exemplary magnet apparatus 124 include respective magnetic elements 146a and 146b (FIG. 6) formed from a ferromagnetic material (e.g., N35 grade neodymium) and thin hermetically sealed housings 148a and 148b formed from, for example, biocompatible metals and/or plastics. Such housing materials may, in some instances, be non-magnetic or paramagnetic. Suitable materials include, but are not limited to, titanium or titanium alloys, polyether ether ketone (PEEK), low-density polyethylene (LDPE), high-density polyethylene (HDPE) and polyamide. In particular, exemplary metals include commercially pure titanium (e.g., Grade 2) and the titanium alloy Ti-6Al-4V (Grade 5). With respect to the overall size of the magnet apparatus 124, the top diameter may be about 10.6 to 12.6 mm, the bottom diameter may be about 12.3 to 14.3 mm, and the thickness T (FIG. 9) may be about 2.2 to 3.0 mm. So configured, the width of the magnet portions 126a and 126b, i.e. the dimension perpendicular to the thickness T and to the axis of rotation AR, may be about 5.9 to 6.2 mm. The divider wall 144 adds about 1.0 mm to the diameters in the direction perpendicular to the wall.

Reorientation of the magnet portions 126a and 126b of the exemplary magnet apparatus 124 causes significantly less stress on the dermis and, accordingly, less pain than conventional implant magnets. Such rotation may be imparted by an MRI magnetic field. Prior to rotation when the cochlear implant is in the flat state (FIG. 10), the distance D1 between the skull bone below the cochlear implant and the skin above the implant is relatively small. This distance is approximately the same as distance $D1_{PA}$ (FIG. 3) of the conventional cochlear implant. The distance between the bone and skin increases only slightly by difference ΔD to distance D2 when the implant magnet portions 126a and 126b rotate separately about their own axis of rotation AR (FIG. 9) to the orientation illustrated in FIG. 11, which shows the exemplary cochlear implant in a distended state. Such rotation also causes the portions of the housing 102 that define the magnet pockets 136a and 136b (as well as the pockets themselves) to stretch and distort. The resilience of the housing material will typically drive the implant magnet portions 126a and 126b to their flat-state orientations when the MRI magnetic field is removed. In some instances, however, the clinician may need to press on the skin over the magnet apparatus to drive the magnet portions back to their flat-state orientations.

It should be noted here that for a given rotational magnitude (e.g., about 75 degrees in FIGS. 4 and 11), the distances ΔD and D2 (FIG. 11) associated with the implant magnet portions 126a and 126b are considerably less than the distances $ΔD_{PA}$ and $D2_{PA}$ (FIG. 4) of the conventional cochlear implant magnet 24. This difference stems from the fact that the width W of the magnet portions 126a and 126b is far smaller than the diameter of the convention disk-shaped magnet 24.

Figure 12:
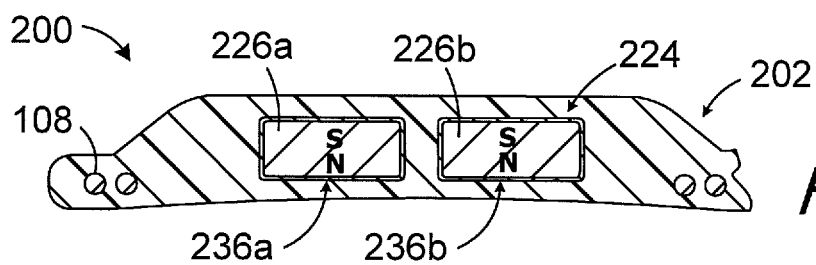
FIG. 12 is a section view of a cochlear implant in accordance with one embodiment of a present invention.
Figure 13:
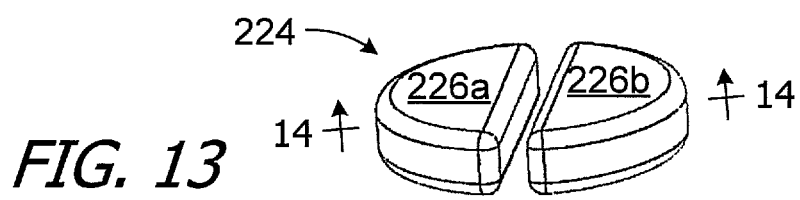
FIG. 13 is a perspective view of a portion of the cochlear implant illustrated in FIG. 12.
Figure 14:
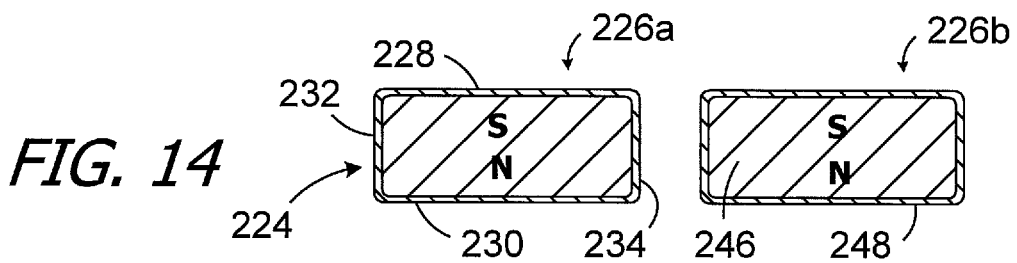
FIG. 14 is a section view taken along line 14-14 in FIG. 13.

The present magnet assembles (and associated magnet portions) are not limited to the configuration illustrated in FIGS. 5-11. To that end, the exemplary cochlear implant 200 illustrated in FIGS. 12-14 is identical to the implant 100 but for the magnet apparatus 224 and slightly differently shaped pockets 236a and 236b in housing 202. The magnet apparatus 224 has an overall cylindrical disk shape (as opposed to a frustoconical disk shape) defined by partial disk shaped magnet portions 226a and 226b. The magnet portions 226a and 226b are identical to one another and each include a partial disk shaped top surface 228, a partial disk shaped bottom surface 230, an outer side surface 232, and an inner side surface 234. In a cross-section perpendicular to the inner side surfaces 234, the magnet portions have a rectangular shape (with rounded corners). The magnet portions 226a and 226b also each include a magnetic element 246 and a thin hermetically sealed housing 248 formed from the materials described above. When exposed to an MRI magnetic field, the magnet apparatus 224 will behave in the manner described above with reference to FIGS. 10 and 11.

Figure 15:
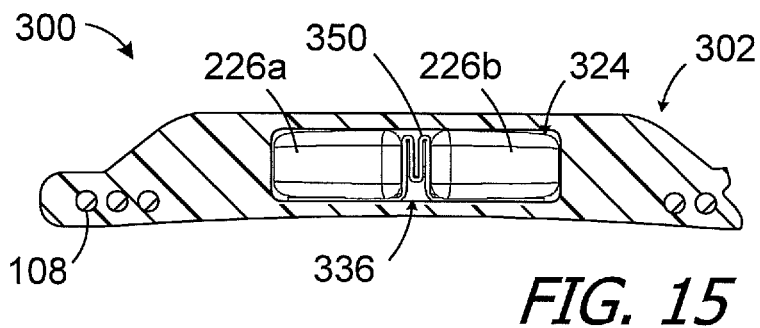
FIG. 15 is a partial section view of a cochlear implant in accordance with one embodiment of a present invention.
Figure 16:
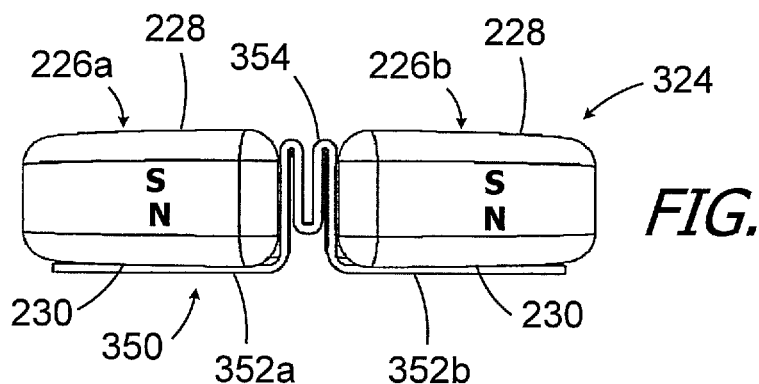
FIG. 16 is a side view of a portion of the cochlear implant illustrated in FIG. 15.
Figure 17:
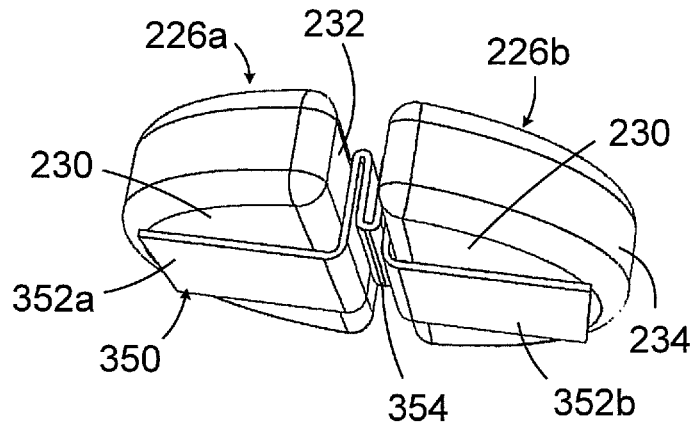
FIG. 17 is a perspective view of a portion of the cochlear implant illustrated in FIG. 15.

Turning to FIGS. 15-17, the exemplary cochlear implant 300 is similar to cochlear implant 200 and similar elements are represented by similar reference numerals. Here, however, the magnet apparatus 324 includes two partial disk shaped magnet portions 226a and 226b that are tethered to one another in a manner that allows magnet portions 226a and 226b to rotate, but limits the rotation to a predetermined amount. The housing 302 includes a single magnet pocket 336 to accommodate tethered arrangement. In the illustrated implementation, the magnet portions 226a and 226b are tethered to one another with a flexible strap 350. The flexible strap 350 includes end portions 352a and 352b, which are respectively secured to the magnet portions 226a and 226b, and an intermediate portion 354 that is not secured to either magnet portion. For example, the end portions 352a and 352b may be secured to the bottom surfaces 230 of the magnet portions 226a and 226b with an adhesive or other suitable instrumentality. The end portions 352a and 352b are not secured to any other surfaces. In other implementations, the end portions 352a and 352b may be secured to more than one surface of one or both of the magnet portions 226a and 226b and/or may be secured to different surfaces (or sets of surfaces) on the magnet portions 226a and 226b. Suitable materials for the flexible strap 250 include, but are not limited to, a nylon cloth strap or Kapton® (polyimide film) tape, including those with reinforcing fibers (e.g., Kevlar® or polyethylene fibers). It should also be noted here that the housing 302 may be formed in two steps, with a bottom cap overmolded onto the remainder of the housing (and formed from the same material as the remainder of the housing) after the tethered magnet portions 226a and 226b have been inserted into the pocket 336.

Figure 18:
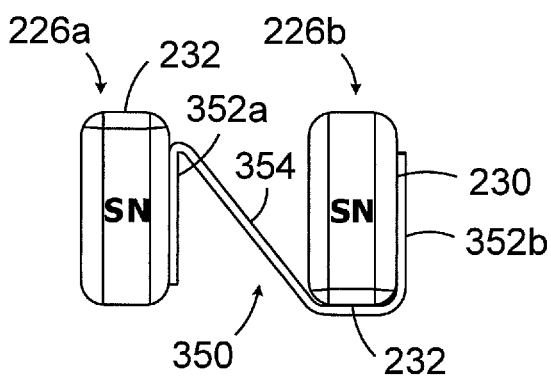
FIG. 18 is a side view of a portion of the cochlear implant illustrated in FIG. 15 in a partially rotated state.
Figure 19:
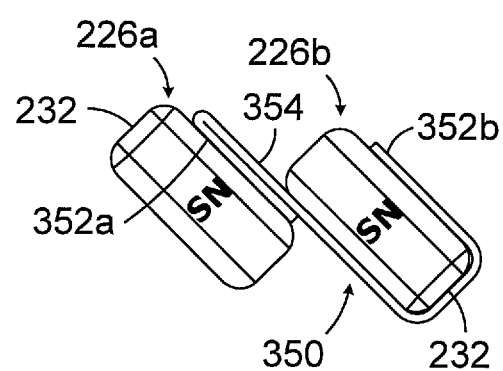
FIG. 19 is a side view of a portion of the cochlear implant illustrated in FIG. 15 in a partially rotated state.

Although the amount of allowed rotation may vary from one implementation to another, the flexible strap 350 in the illustrated implementation allows the magnet portions 226a and 226b to rotate up to approximately 135 degrees form the flat-state orientation illustrated in FIGS. 15-17 in response to the presence of an MRI magnetic field. The magnet portions 226a and 226b may, for example, rotate to the orientation illustrated in FIG. 18 in some instances. Rotation beyond the orientation illustrated in FIG. 19 is, however, prevented by the strap 250. As a result, an MRI magnetic field will not cause the N-S orientations of the magnet portions 226a and 226b to be completely reversed.

Figure 20:
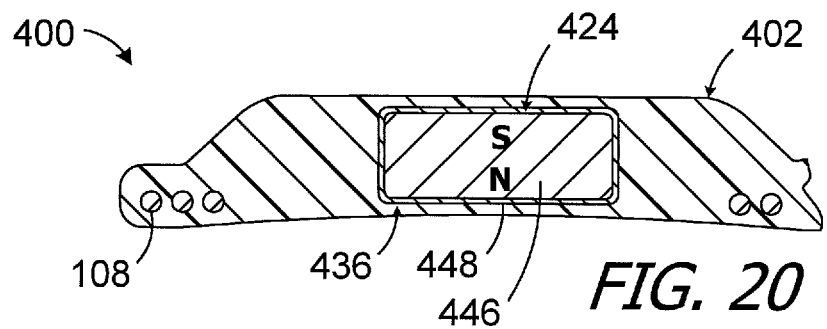
FIG. 20 is a section view of a cochlear implant in accordance with one embodiment of a present invention.
Figure 21:
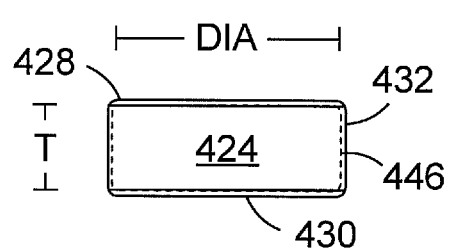
FIG. 21 is a side view of a portion of the cochlear implant illustrated in FIG. 20.
Figure 22:
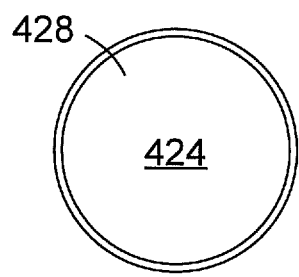
FIG. 22 is a plan view of a portion of the cochlear implant illustrated in FIG. 20.

Referring to FIGS. 20-23, the stress on the skin (and associated pain) may also be reduced by employing particular magnet diameter to thickness ratios ("D/T ratios"). To that end, the exemplary cochlear implant 400 illustrated in FIG. 20 is similar to cochlear implant 300 and similar elements are represented by similar reference numerals. Here, however, the magnet apparatus 424 is a unitary structure which does not include a pair of magnet portions. The magnet apparatus 424 has a cylindrical disk shape and includes a circular top surface 428, a circular bottom surface 430, and an outer side surface 432, and is formed from a magnetic element 446 and a thin hermetically sealed housing 448 that covers the outer surface of, and has the same overall shape as, the magnetic element. In a cross-section through the diameter, the magnet apparatus 424 has a rectangular shape (with rounded corners).

The exemplary magnetic element 446 may have a DtoT ratio of 2.5 or less. To that end, the exemplary magnetic element 446 has a diameter DIA of 7.1 mm, a thickness T of 2.8 mm, and a DtoT ratio of 2.5. In another exemplary embodiment, the magnetic element may have a diameter DIA of 6.5 mm, a thickness T of 3.5 mm, and a DtoT ratio of 1.9. In other embodiments, the DtoT ratio may range from 2.5 to 1.9, with magnetic element diameters of 7.1 or less, and magnet thicknesses of 2.8 or more. The dimensions magnet apparatus also include the thin housing 448, which adds about 0.2 to 0.3 mm to the diameters and thicknesses discussed above. For purposes of comparison, the conventional magnet 24 illustrated in FIGS. 1-4, which has a diameter of 10.5 mm and a thickness of 2.2 mm, has a DtoT ratio of 4.8. Suitable material for the magnetic element 446 includes N52 grade neodymium, and suitable materials for the housing 448 include the housing materials described above.

Figure 23:
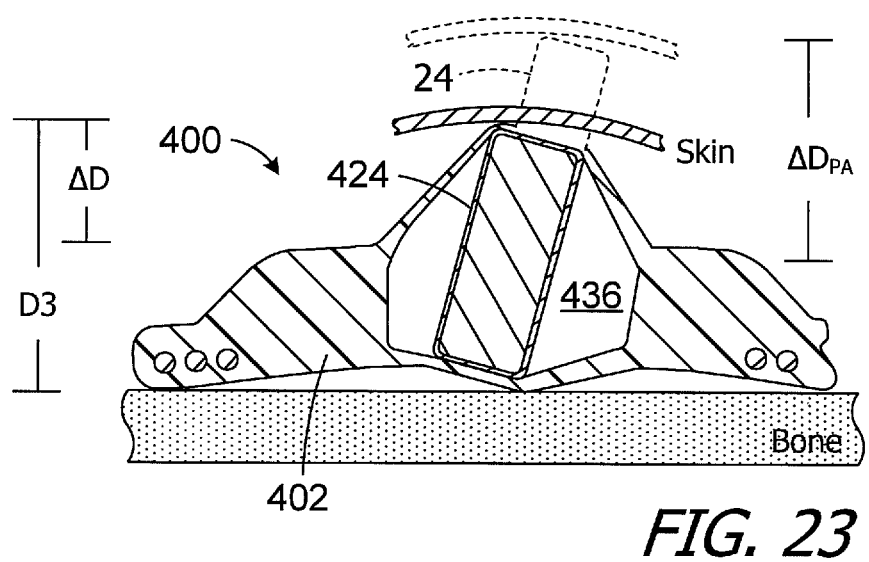
FIG. 23 is a section view showing the result of an application of a MRI magnetic field to the cochlear implant illustrated in FIG. 20.

Referring to FIG. 23, the magnet apparatus 424 will rotate in a manner similar to the conventional magnet 24 when exposed to an MRI magnetic field. However, the distances $\Delta D$ and D3 associated with the magnet apparatus 424 are considerably less than the distances $\Delta D_{PA}$ and $D2_{PA}$ of the conventional cochlear implant. This difference stems from the fact that the diameter of the magnet apparatus 424 is smaller than the diameter of the convention disk-shaped magnet 24. As a result, reorientation of the magnet apparatus 424 causes significantly less stress on the dermis and, accordingly, less pain than the conventional implant magnet 24.

Figure 24:
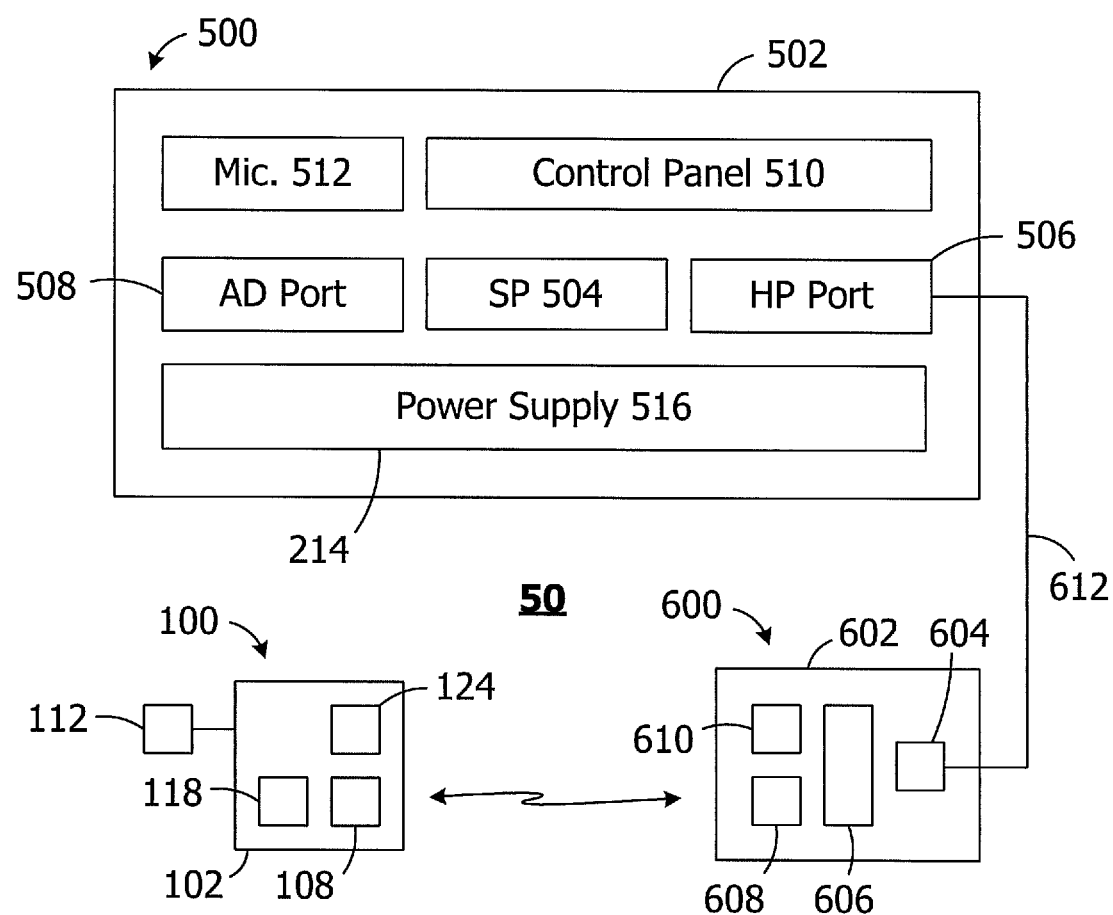
FIG. 24 is a block diagram of a cochlear implant system in accordance with one embodiment of a present invention.

As illustrated in FIG. 24, the exemplary cochlear implant system 50 includes the cochlear implant 100 (or 200 or 300 or 400), a sound processor, such as the illustrated body worn sound processor 200 or a behind-the-ear sound processor, and a headpiece 300.

The exemplary body worn sound processor 500 in the exemplary ICS system 50 includes a housing 502 in which and/or on which various components are supported. Such components may include, but are not limited to, sound processor circuitry 504, a headpiece port 506, an auxiliary device port 508 for an auxiliary device such as a mobile phone or a music player, a control panel 510, one or microphones 512, and a power supply receptacle 514 for a removable battery or other removable power supply 516 (e.g., rechargeable and disposable batteries or other electrochemical cells). The sound processor circuitry 504 converts electrical signals from the microphone 512 into stimulation data. The exemplary headpiece 600 includes a housing 602 and various components, e.g., a RF connector 604, a microphone 606, an antenna (or other transmitter) 608 and a positioning magnet apparatus 610, that are carried by the housing. The magnet apparatus 610 may consist of a single magnet or may consist of one or more magnets and a shim. The headpiece 600 may be connected to the sound processor headpiece port 506 by a cable 612. The positioning magnet apparatus 610 is attracted to the magnet apparatus 124 of the cochlear stimulator 100, thereby aligning the antenna 608 with the antenna 108. The stimulation data and, in many instances power, is supplied to the headpiece 600. The headpiece 600 transcutaneously transmits the stimulation data, and in many instances power, to the cochlear implant 100 by way of a wireless link between the antennas. The stimulation processor 118 converts the stimulation data into stimulation signals that stimulate the electrodes 114 of the electrode array 112.

In at least some implementations, the cable 612 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone(s) 512 on the sound processor 500, the microphone 606 may be also be omitted in some instances. The functionality of the sound processor 500 and headpiece 600 may also be combined into a single head wearable sound processor. Examples of head wearable sound processors are illustrated and described in U.S. Pat. Nos. 8,811,643 and 8,983,102, which are incorporated herein by reference in their entirety.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A cochlear implant, comprising:
a cochlear lead including a plurality of electrodes;
a flexible housing;
a magnet apparatus, located within the flexible housing, including a first partial disk shaped magnet member and a second partial disk shaped magnet member spaced apart from the first partial disk shaped magnet member, the first partial disk shaped magnet member defining a first axis of rotation and the second partial disk shaped magnet member defining a second axis of rotation that is spaced apart from the first axis of rotation;
an antenna within the flexible housing and adjacent to the magnet apparatus; and
a stimulation processor operably connected to the antenna and to the cochlear lead.

2. A cochlear implant as claimed in claim 1, wherein the antenna and the first and second magnet members are embedded in the flexible housing.

3. A cochlear implant as claimed in claim 1, wherein the flexible housing is formed from a silicone elastomer.

4. A cochlear implant as claimed in claim 1, wherein the flexible housing includes a top wall above the magnet pocket that does not include an opening into the magnet pocket and a bottom wall below the magnet pocket that does not include an opening into the magnet pocket.

5. A cochlear implant as claimed in claim 1, wherein the magnet apparatus defines either a frustoconical shape or a cylindrical shape.

6. A cochlear implant as claimed in claim 1, wherein the flexible housing defines separate first and second magnet pockets;
the first partial disk shaped magnet member is located within the first magnet pocket; and
the second partial disk shaped magnet member is located within the second magnet pocket.

7. A cochlear implant as claimed claim 1, wherein the first and second partial disk shaped magnet members are tethered to one another.

8. A cochlear implant as claimed in claim 7, wherein the first and second partial disk shaped magnet members are tethered to one another by a flexible strap that limits rotation of the first and second partial disk shaped magnet members.

9. A cochlear implant as claimed in claim 8, wherein the flexible strap includes a first strap portion that is secured to the first partial disk shaped magnet member, a second strap portion that is secured to the second partial disk shaped magnet member, and a third strap portion that is not secured to either of the first and second partial disk shaped magnet members.

10. A cochlear implant as claimed in claim 1, wherein the first partial disk shaped magnet member defines a N-S orientation; and
the second partial disk shaped magnet member defines a N-S orientation that is the same as the N-S orientation of the first partial disk shaped magnet member.

11. A system, comprising
a cochlear implant as claimed in claim 1; and
a headpiece including
an antenna, and
a headpiece magnet associated with the antenna that is attracted to the implant magnet.

12. A system, comprising
a cochlear implant as claimed in claim 1;
a sound processor; and
a headpiece, operably connected to the sound processor, including
an antenna, and
a headpiece magnet associated with the antenna that is attracted to the implant magnet.

13. A cochlear implant, comprising:
a cochlear lead including a plurality of electrodes;
a flexible housing;
a magnet apparatus, located within the flexible housing, including a first partial disk shaped magnet member and a second partial disk shaped magnet member spaced apart from the first partial disk shaped magnet member, the first partial disk shaped magnet member defining a first axis of rotation and the second partial disk shaped magnet member defining a second axis of rotation that is spaced apart from the first axis of rotation;
an antenna within the flexible housing and adjacent to the magnet apparatus; and
a stimulation processor operably connected to the antenna and to the cochlear lead;
wherein the respective configurations of the flexible housing and the first and second partial disk shaped magnet members are such that the first and second partial disk shaped magnet members will rotate independently and distort the flexible housing in response to the presence of a magnetic field of at least 1.5 T.

14. A cochlear implant as claimed in claim 13, wherein the antenna and the first and second magnet members are embedded in the flexible housing.

15. A cochlear implant as claimed in claim 13, wherein the flexible housing is formed from a silicone elastomer.

16. A cochlear implant as claimed in claim 13, wherein the flexible housing includes a top wall above the magnet pocket that does not include an opening into the magnet pocket and a bottom wall below the magnet pocket that does not include an opening into the magnet pocket.

17. A cochlear implant as claimed in claim 13, wherein the magnet apparatus defines either a frustoconical shape or a cylindrical shape.

18. A cochlear implant as claimed in claim 13 wherein the flexible housing defines separate first and second magnet pockets;
the first partial disk shaped magnet member is located within the first magnet pocket; and
the second partial disk shaped magnet member is located within the second magnet pocket.

19. A cochlear implant as claimed claim 13, wherein the first and second partial disk shaped magnet members are tethered to one another.

20. A cochlear implant as claimed in claim 19, wherein the first and second partial disk shaped magnet members are tethered to one another by a flexible strap that limits rotation of the first and second partial disk shaped magnet members.

\* \* \* \* \*